United States Patent
Hall et al.

(10) Patent No.: US 10,285,756 B2
(45) Date of Patent: May 14, 2019

(54) BENDABLE CATHETER ARMS HAVING VARIED FLEXIBILITY

(71) Applicant: St. Jude Medical, Atrial Fibrillation Division, Inc., St. Paul, MN (US)

(72) Inventors: Sacha C. Hall, Doral, FL (US); Dale E. Just, Minneapolis, MN (US); Alan de la Rama, Cerritos, CA (US); Cary Hata, Irvine, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 0 days.

(21) Appl. No.: 15/232,583

(22) Filed: Aug. 9, 2016

(65) Prior Publication Data

US 2016/0346040 A1 Dec. 1, 2016

Related U.S. Application Data

(60) Division of application No. 14/081,666, filed on Nov. 15, 2013, now Pat. No. 9,408,663, which is a continuation of application No. 13/072,357, filed on Mar. 25, 2011, now Pat. No. 8,588,885, which is a continuation-in-part of application No. 12/599,035, (Continued)

(51) Int. Cl.
| | |
|---|---|
| *A61B 5/04* | (2006.01) |
| *A61B 18/14* | (2006.01) |
| *A61B 5/042* | (2006.01) |
| *A61B 5/00* | (2006.01) |
| *A61B 18/00* | (2006.01) |

(52) U.S. Cl.
CPC ........ *A61B 18/1492* (2013.01); *A61B 5/0422* (2013.01); *A61B 5/4836* (2013.01); *A61B 5/6858* (2013.01); *A61B 2018/00267* (2013.01); *A61B 2018/00351* (2013.01); *A61B 2018/00577* (2013.01); *A61B 2018/00839* (2013.01)

(58) Field of Classification Search
CPC .......................... A61B 5/0422; A61B 18/1492
See application file for complete search history.

(56) References Cited

U.S. PATENT DOCUMENTS

| | | |
|---|---|---|
| 4,940,064 A | 7/1990 | Desai |
| 5,345,936 A | 9/1994 | Pomeranz et al. |

(Continued)

FOREIGN PATENT DOCUMENTS

| | | |
|---|---|---|
| WO | 1996034560 A1 | 11/1996 |
| WO | 2006058251 A2 | 6/2006 |
| WO | 2008141150 A2 | 11/2008 |

*Primary Examiner* — Lee S Cohen
(74) *Attorney, Agent, or Firm* — Dykema Gossett PLLC

(57) ABSTRACT

In various embodiments, a catheter comprising an expandable electrode assembly or basket is provided. In specific embodiments, the basket is particularly useful for mapping electrical activity at one or more locations within the heart. The basket can comprise a plurality of bendable or deflectable arms. At least one of the arms may have varied flexibility over its length in the form of one or more discontinuities of stiffness or flexibility at an elbow region or other variances in flexibility over the arm's length. Such variance in flexibility may allow the arm to assume a different bent configuration or respond to external factors more positively than possible with an arm having a static or near static flexibility or stiffness over its length.

16 Claims, 14 Drawing Sheets

Related U.S. Application Data filed as application No. PCT/US2008/063204 on May 9, 2008, now Pat. No. 8,224,416.

(60) Provisional application No. 60/917,053, filed on May 9, 2007.

(56) References Cited

U.S. PATENT DOCUMENTS

| | | | |
|---|---|---|---|
| 5,400,783 | A | 3/1995 | Pomeranz et al. |
| 5,411,025 | A | 5/1995 | Webster, Jr. |
| 5,425,364 | A * | 6/1995 | Imran ............ A61B 5/0422 600/374 |
| 5,465,717 | A * | 11/1995 | Imran ............ A61B 5/0422 600/374 |
| 5,471,982 | A | 12/1995 | Edwards et al. |
| 5,531,686 | A | 7/1996 | Lundquist et al. |
| 5,549,661 | A | 8/1996 | Kordis et al. |
| 5,628,313 | A | 5/1997 | Webster, Jr. |
| 5,647,870 | A | 7/1997 | Kordis et al. |
| 5,702,438 | A | 12/1997 | Avitall |
| 5,722,401 | A * | 3/1998 | Pietroski ......... A61B 5/0422 600/374 |
| 5,730,128 | A | 3/1998 | Pomeranz et al. |
| 5,782,239 | A | 7/1998 | Webster, Jr. |
| 5,855,552 | A | 1/1999 | Houser et al. |
| 5,871,483 | A | 2/1999 | Jackson et al. |
| 5,893,847 | A | 4/1999 | Kordis |
| 5,904,680 | A | 5/1999 | Kordis et al. |
| 5,925,038 | A | 7/1999 | Panescu et al. |
| 5,928,228 | A | 7/1999 | Kordis et al. |
| 6,014,579 | A | 1/2000 | Pomeranz et al. |
| 6,016,437 | A | 1/2000 | Tu et al. |
| 6,071,282 | A | 6/2000 | Fleischman |
| 6,119,030 | A | 9/2000 | Morency |
| 6,216,043 | B1 | 4/2001 | Swanson et al. |
| 6,741,878 | B2 | 5/2004 | Fuimaono et al. |
| 6,748,255 | B2 | 6/2004 | Fuimaono et al. |
| 6,805,131 | B2 | 10/2004 | Kordis |
| 6,973,340 | B2 | 12/2005 | Fuimaono et al. |
| 7,149,563 | B2 | 12/2006 | Fuimaono et al. |
| 7,245,955 | B2 | 7/2007 | Rashidi |
| 7,257,434 | B2 | 8/2007 | Fuimaono et al. |
| 7,269,453 | B2 | 9/2007 | Mogul |
| 7,291,146 | B2 | 11/2007 | Steinke et al. |
| 7,429,261 | B2 | 9/2008 | Kunis et al. |
| 7,468,062 | B2 | 12/2008 | Oral et al. |
| 7,474,909 | B2 | 1/2009 | Phan et al. |
| 7,615,049 | B2 | 11/2009 | West et al. |
| 7,850,685 | B2 | 12/2010 | Kunis et al. |
| 7,993,333 | B2 | 8/2011 | Oral et al. |
| 8,103,327 | B2 | 1/2012 | Harlev et al. |
| 8,224,416 | B2 | 7/2012 | de la Rama et al. |
| 8,380,275 | B2 | 2/2013 | Kim et al. |
| 8,588,885 | B2 * | 11/2013 | Hall ............ A61B 5/0422 600/374 |
| 9,408,663 | B2 * | 8/2016 | Hall ............ A61B 5/0422 |
| 2002/0138075 | A1 | 9/2002 | Edwards et al. |
| 2003/0114739 | A1 | 6/2003 | Fuimaono et al. |
| 2004/0133091 | A1 | 7/2004 | Fuimaono et al. |
| 2006/0009690 | A1 | 1/2006 | Fuimaono et al. |
| 2006/0089637 | A1 | 4/2006 | Werneth et al. |
| 2006/0106375 | A1 | 5/2006 | Werneth et al. |
| 2007/0276212 | A1 | 11/2007 | Fuimaono et al. |
| 2009/0182325 | A1 | 7/2009 | Werneth et al. |
| 2011/0213231 | A1 | 9/2011 | Hall et al. |
| 2013/0253298 | A1 * | 9/2013 | Harlev ............ A61B 5/0422 600/374 |

\* cited by examiner

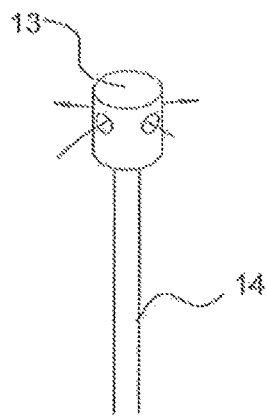
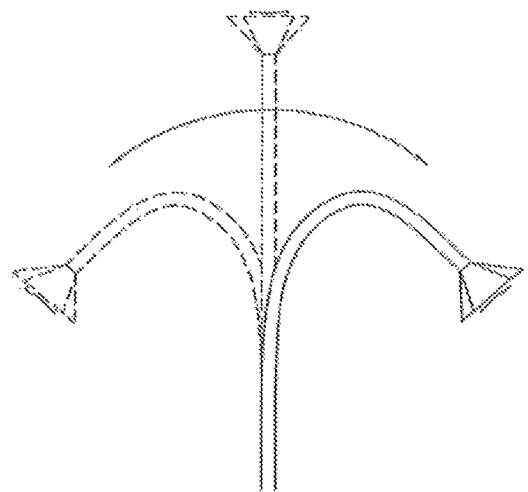
FIG. 5
FIG. 6 A
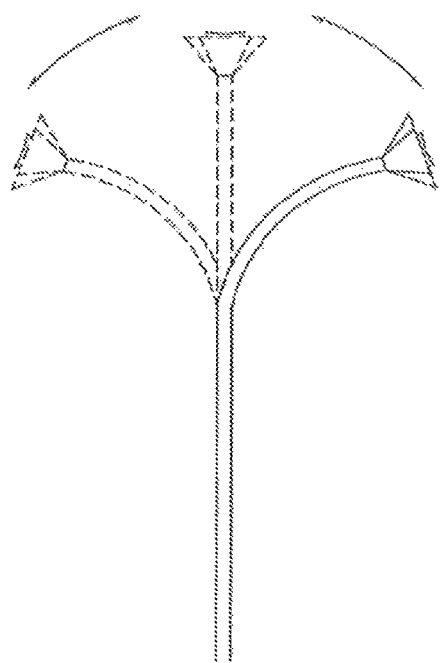
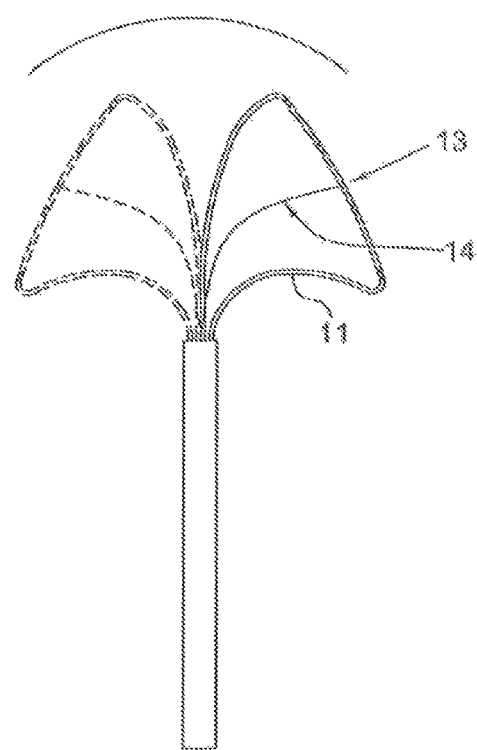
FIG. 6 B
FIG. 7

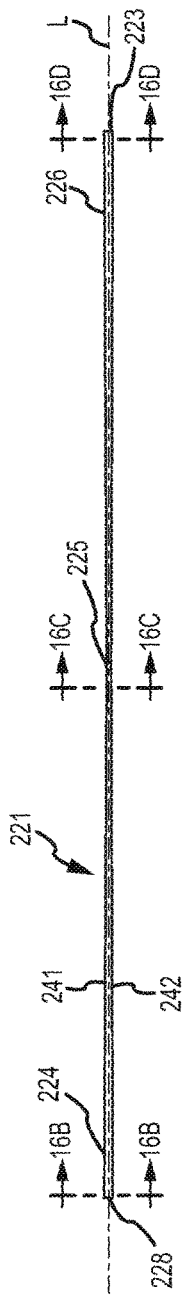
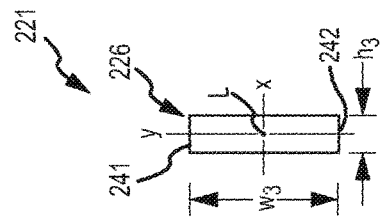
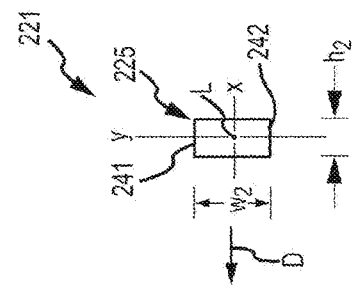
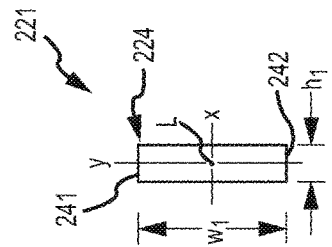

BENDABLE CATHETER ARMS HAVING VARIED FLEXIBILITY

CROSS-REFERENCE TO RELATED APPLICATIONS

This application is a divisional of U.S. application Ser. No. 14/081,666, filed 15 Nov. 2015 (the '666 application), now U.S. Pat. No. 9,408,663, which is a continuation of U.S. application Ser. No. 13/072,357, filed 25 Mar. 2011 (the '357 application), now U.S. Pat. No. 8,588,885, which is a continuation-in-part of U.S. application Ser. No. 12/599,035, filed 9 May 2008 (the '035 application), now U.S. Pat. No. 8,224,416, which is the national stage of international application no. PCT/US08/63204, with an international filing date of 9 May 2008 (the '204 application), which claims priority to and the benefit of U.S. provisional application No. 60/917,053, filed on 9 May 2007 (the '053 application). The '357 application, the '035 application, the '204 application, and the '053 application are each hereby incorporated by reference as though fully set forth herein.

BACKGROUND OF THE INVENTION a. Field of the Invention

The present invention pertains generally to catheters and electrode assemblies. More particularly, the present invention is directed toward mapping catheters including high density mapping catheters, and ablation catheters.

b. Background Art

Electrophysiology catheters are used for an ever-growing number of procedures. For example, catheters are used for diagnostic, therapeutic, and ablative procedures, to name just a few examples. Typically, the catheter is manipulated through the patient's vasculature and to the intended site, for example, a site within the patient's heart. The catheter typically carries one or more electrodes, which may be used for ablation, diagnosis, or the like. There are a number of methods used for ablation of desired areas, including for example, radiofrequency (RF) ablation. RF ablation is accomplished by transmission of radiofrequency energy to a desired target area through an electrode assembly to ablate tissue at the target site.

By mapping the electrical activities using mapping electrodes of a catheter, one can detect ectopic sites of electrical activation or other electrical activation pathways that contribute to cardiac disorders. This type of information is very valuable and allows a cardiologist to locate and treat dysfunctional cardiac tissues. Ablation electrodes can be provided on a catheter for ablating cardiac tissue. Ablation is considered a field within electrophysiology and is important because it obviates the need for more invasive and risky surgical treatments such as open heart surgery.

Typically, the electrode catheter is inserted into a major vein or artery, and then guided into the heart chamber of concern. Due to the unpredictability of the interior size and shape of an individual's heart and the location of the area of concern, the ability to control the exact position and orientation of the catheter is essential and critical to the effectiveness of the ablation treatment by electrode catheter.

Such electrophysiological ablation and mapping catheters typically have an elongated flexible body with a distal end that carries one or more electrodes that are used to map or collect electrical information about electrical activities in the heart. Typically, the distal end is steerable to provide the user the ability to adequately guide and position the catheter to the desired location. Some types of electrode ablation and mapping catheters (see, e.g., U.S. Pat. No. 7,027,851, which is hereby incorporated by reference in its entirety) use multiple electrode arms or spines to allow multiple measurements to be taken at once, thereby reducing the time it takes to map the heart. Although such types of electrode ablation and mapping catheters make mapping more efficient, they suffer from the lack of control over the individual electrode spines or arms. In addition, because of the unpredictable and often irregular shapes and sizes of the inner-heart, such uncontrollable independent configuration of electrode spines or arms often lead to unreliable mapping and ablation, because the user cannot adequately predict or control where a particular electrode spine or arm will be positioned relative to another electrode spine or arm. Accordingly, the need exists for an improved catheter that can more effectively control and position multiple electrode members and increase location predictability of electrode members, while being steerable and deflectable.

BRIEF SUMMARY OF THE INVENTION

In various embodiments, a catheter comprising an expandable electrode assembly or basket is provided. In specific embodiments, the basket is particularly useful for mapping electrical activity at one or more locations within the heart. The basket can comprise a plurality of bendable or deflectable arms. At least one of the arms can have varied flexibility over its length in the form of one or more discontinuities of stiffness or flexibility at an elbow region or other variances in flexibility over the arm's length. Such variance in flexibility can allow the arm to assume a different bent configuration or respond to external factors more positively than possible with an arm having a static or near static flexibility or stiffness over its length.

Accordingly, in at least one embodiment, the catheter can comprise an elongated body having a proximal end and a distal end and an electrode assembly at the distal end of the elongated body. In these embodiments, the electrode assembly can comprise a plurality of arms, each having a proximal end connected to the distal end of the elongated body and a distal end. Further, the distal ends of the arms can be connected at a tip junction. Moreover, the electrode assembly is collapsible to a collapsed arrangement to fit within a lumen of a shaft and is also expandable to an expanded arrangement. Additionally, at least one of the arms comprises at least one electrode and a support member. In these embodiments, the support member can further comprise a distal portion, a proximal portion, and an intermediate portion therebetween. One of the distal and proximal portions can define a first width and the intermediate portion can define a second width, where the first width is greater than the second width. Accordingly, the flexibility of the intermediate portion can be enhanced or greater than the flexibility of the distal and/or proximal portions. Stated otherwise, the stiffness of the distal and/or proximal portions can be greater than the stiffness of the intermediate portion.

In various embodiments, an arm for an expandable catheter basket or electrode assembly is provided. The arm can comprise a bendable support member defining a distal portion, a proximal portion, and an intermediate portion therebetween. The arm can further comprise means for enhancing flexibility of the intermediate portion relative to one or both of the distal and proximal portions and at least one electrode positioned along the support member. Such embodiments can provide an arm that is able to resist undesirable inversion when expanded or arched and in use.

In at least one embodiment, the means for enhancing flexibility can be provided by the support member being narrower at the intermediate portion than the distal and/or proximal portions. Alternatively, in at least one embodiment, the means for enhancing flexibility can be provided by openings located in the intermediate portion. In other alternate embodiments, the means for enhancing flexibility can be provided by composite material layers and/or by varying the material composition between the intermediate portion and the distal and/or proximal portions such that the flexibility of the intermediate portion is greater than the flexibility of the distal and/or proximal portions.

In various embodiments, an arm for an expandable catheter basket or electrode assembly is provided. The arm can comprise a bendable support member defining a distal portion, a proximal portion, and an intermediate portion therebetween. The arm can further comprise means for enhancing flexibility of the distal and proximal portions relative to the intermediate portion and at least one electrode positioned along the support member. Such embodiments can provide an arm that is able to bow, splay, or bulge outwardly more than otherwise possible at least over the distal and/or proximal portions when expanded or arched, thereby favorably positioning the electrode(s), particularly any electrode(s) located at or near the distal or proximal portions of the support member.

In at least one embodiment, the means for enhancing flexibility can be provided by the distal and proximal portions being tapered on one side or on opposing sides of the support member. Alternatively, in at least one embodiment, the means for enhancing flexibility can be provided by openings located in the distal and/or proximal portions. In other alternative embodiments, the means for enhancing flexibility can be provided by composite material layers and/or by varying the material composition between the intermediate portion and the distal and/or proximal portions such that the flexibility of the distal and/or proximal portions is greater than the flexibility of the intermediate portion.

The foregoing and other aspects, features, details, utilities, and advantages of the present invention will be apparent from reading the following description and claims, and from reviewing the accompanying drawings.

BRIEF DESCRIPTION OF THE DRAWINGS

FIG. 5 is a perspective view of the tip junction of the electrode assembly of a catheter according to an embodiment of the invention.

FIGS. 6A and 6B are side views of two catheter shafts showing different degrees of shaft deflection.

FIG. 7 is a side view of the distal region of a catheter shaft showing the tilting of the electrode assembly using an adjusting member attached to the tip junction.

FIG. 16A is a top view of a bendable support member, according to at least one embodiment.

FIG. 16B is a cross-sectional view of a distal portion of the bendable support member of FIG. 16A, taken along line 16B-16B.

FIG. 16C is a cross-sectional view of an intermediate portion of the bendable support member of FIG. 16A, taken along line 16C-16C.

FIG. 16D is a cross-sectional view of a proximal portion of the bendable support member of FIG. 16D, taken along line 16D-16D.

DETAILED DESCRIPTION OF EMBODIMENTS OF THE INVENTION

Certain exemplary embodiments will now be described to provide an overall understanding of the principles of the structure, function, manufacture, and use of the devices and methods disclosed herein. One or more examples of these embodiments are illustrated in the accompanying drawings. Those of ordinary skill in the art will understand that the devices and methods specifically described herein and illustrated in the accompanying drawings are non-limiting exemplary embodiments and that the scope of the various embodiments of the present disclosure is defined solely by the claims. The features illustrated or described in connection with one exemplary embodiment may be combined with the features of other embodiments. Such modifications and variations are intended to be included within the scope of the present disclosure.

Figure 1:
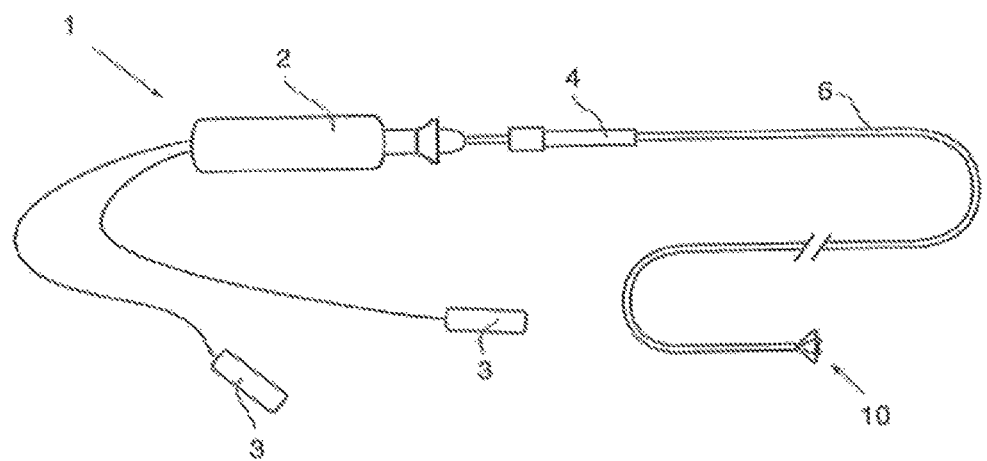
FIG. 1 is a perspective view of a catheter system according to an embodiment of the present invention.

FIG. 1 is a perspective view of a catheter system 1 according to an embodiment of the present invention. The catheter system 1 includes a handle 2 and connectors 3 disposed proximal to the handle 2 for making electrical connections to an electronic mapping system or the like (not shown). The handle 2 can have a uni-directional design, a bi-directional design, a double bi-directional design, or any other suitable design. The catheter system 1 also has a delivery sheath intro 4 located distal to the handle 2 that a surgeon may use to deliver a sheath 6 into the body of a patient. The sheath 6 extends from the delivery sheath intro 4. Further, an electrode assembly or basket 10 protrudes from the distal end of the sheath 6. As those of ordinary skill in the art will recognize, the handle 2, the delivery sheath intro 4, and electronic connectors 3 may readily be modified as dictated by the aesthetic or functional needs of particular applications.

Figure 2A:
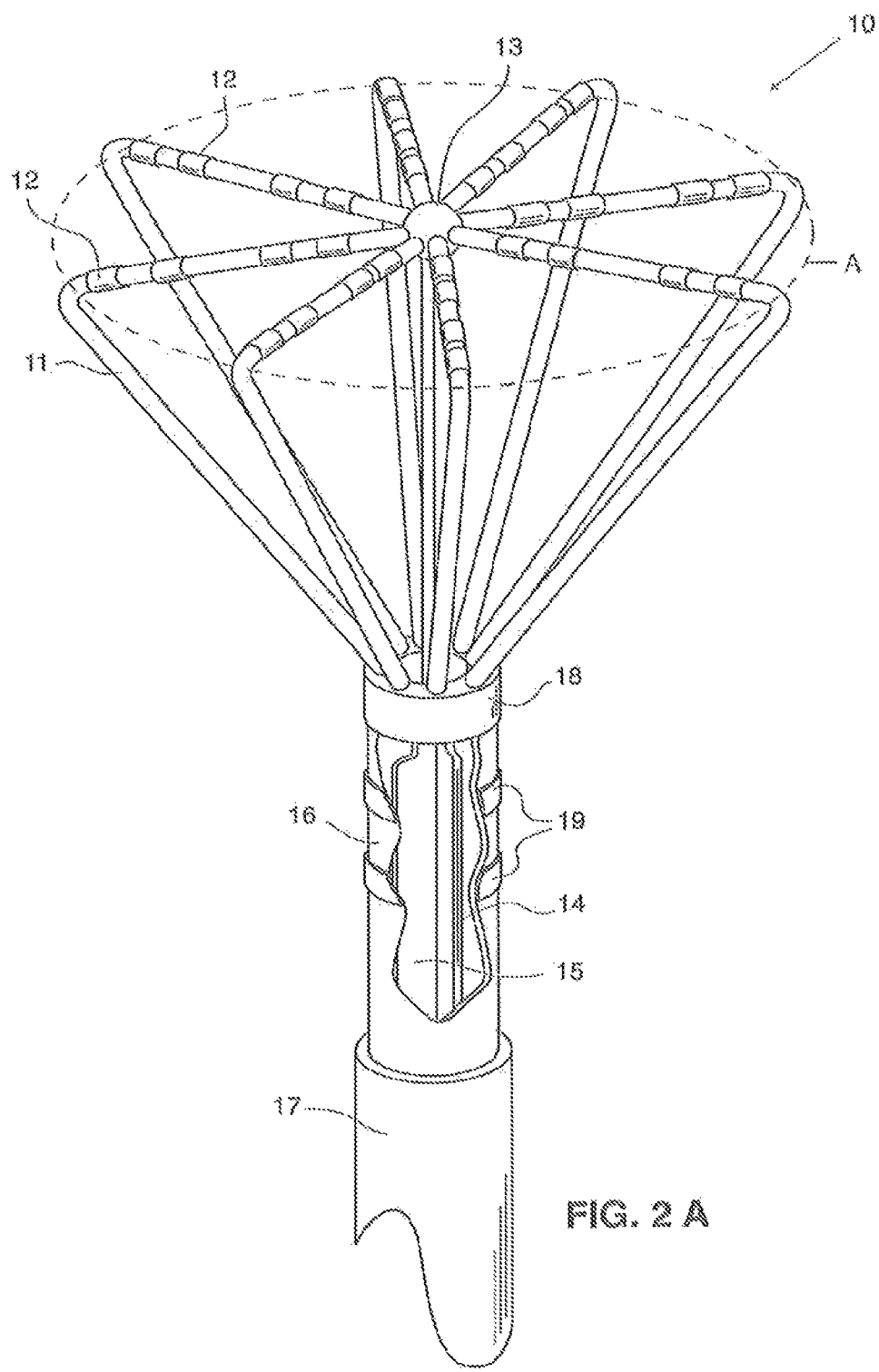
FIG. 2A is a perspective view of a catheter showing an electrode assembly or basket in an expanded profile.
Figure 2:
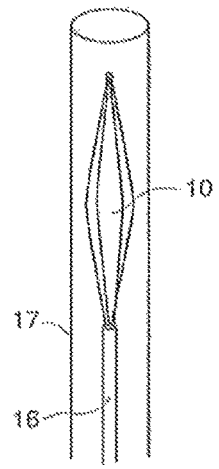
FIG. 2B is a perspective view of the electrode assembly in a collapsed profile inside a sheath.

FIGS. 2A and 2B illustrate the electrode assembly 10 in greater details. FIG. 2A shows the electrode assembly 10 in an expanded profile, while FIG. 2B shows the electrode assembly 10 in a collapsed profile inside a sheath 17. The electrode assembly 10 may be collapsed by a force to the collapsed profile and, upon removal of the force, returns to the expanded profile. This may be achieved by using a shape memory material or some other biasing mechanism. The electrode assembly 10 shown has eight spines 11. Each of the spines 11 has a distal and a proximal end. The spines are deflectable elongated pieces that carry electrodes 12 along a length of the spines 11. In this embodiment, a plurality of electrodes 12 are disposed between the elbow regions 20 (as discussed below in connection with FIGS. 3A-3D) and the distal ends of the spines 11. When the electrode assembly 10 is in the expanded profile, according to this particular embodiment, the electrodes 12 on the spines 11 form an array of electrodes distributed over a substantially flat surface within an area encircled by dashed line A. The electrode assembly 10 has a generally cone shape in the expanded profile. Of course, the array of electrodes 12 need not be distributed over a substantially flat surface but may take on a nonplanar surface profile in the expanded state in other embodiments depending on the application of the electrode assembly. In specific embodiments, the spines 11 include mapping electrodes 12 that are spaced differently among the different spines 11 so as to provide orientation information for the mapping. In other embodiments, an ablation electrode is provided at one or more of the elbows 20 of the spines 11.

The distal ends of the spines 11 are connected at a tip junction 13 (see FIG. 5). The electrode assembly 10 is coupled at its proximal end to a distal end of a longitudinal shaft 16, and the shaft 16 is slidably received within a longitudinal lumen of the sheath 17. In FIG. 2B, the collapsible electrode assembly 10 is in a collapsed profile and is slidably received within the longitudinal lumen of the sheath 17. During delivery of the catheter into the target site within a patient's body, the electrode assembly 10 remains collapsed as shown in FIG. 2B. The electrode assembly 10 expands, as shown in FIG. 2A, when it is pushed through the distal end of the sheath 17 at the target site. The elbows 20 of the spines 11 move radially outwardly and the spine tip junction 13 move closer to the distal end of the catheter shaft 16 as the electrode assembly 10 moves from the collapsed profile to the expanded profile. The electrode assembly 10 is preferably biased from the collapsed state toward the expanded state when the force applied to move it to the collapsed state is removed. As discussed in more detail below, this can be achieved by using shape memory materials or the like.

The tip junction 13 may be a block with a plurality of transverse through holes, as seen in FIG. 5. The transverse through holes receive spines 11. The spines 11 can be fastened to the tip junction 13 by adhesives, welding or other suitable means. The tip junction 13 is connected to the distal end of an adjusting member 14 which may be in the form of a control wire. The adjusting member 14 extends into the shaft 16 and is slidably received within the shaft. The proximal end of the adjusting member 14 is coupled to a user-actuated controller such that movement of the adjusting member 14 in a proximal direction will also move the tip junction 13 in the proximal direction, which in turn causes the electrode assembly 10 to move toward or away from the expanded profile as shown in FIG. 2A and FIG. 3A.

Optionally, the tip junction 13 can be an electrode for mapping and/or ablating. In such an embodiment, the tip junction 13 is electrically connected to a power source and can selectively apply energy, or collect electrical data, or both.

Figure 3:
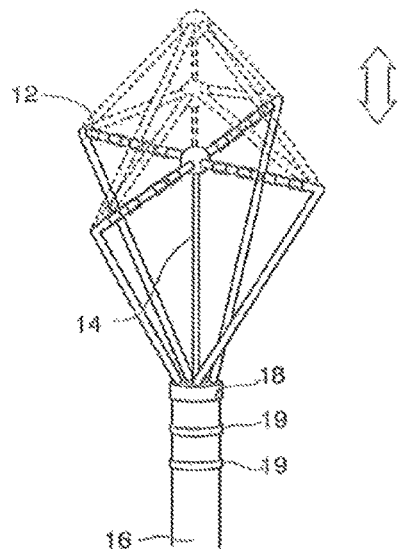
FIGS. 3A-3D illustrate the electrode assembly having spines formed of generally linear spine segments at different stages of expansion from the collapsed profile to the expanded profile, and having electrodes disposed between the elbows and the distal ends of the spines, according to an embodiment of the invention.
FIGS. 3E-3G illustrate an electrode assembly having arcuate shape spines according to another embodiment of the invention.
Figure 3:
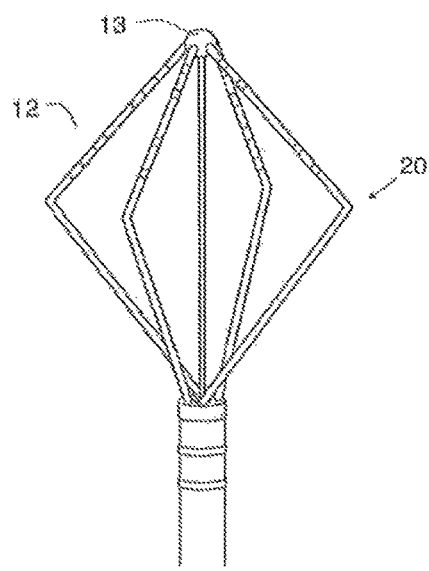
Figure 3:
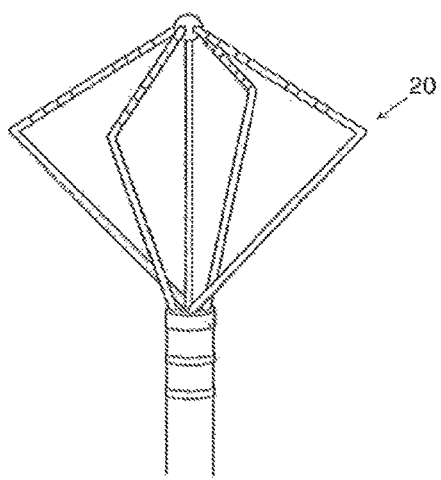
Figure 3:
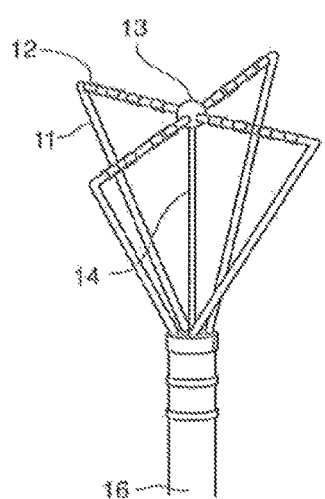
Figure 3:
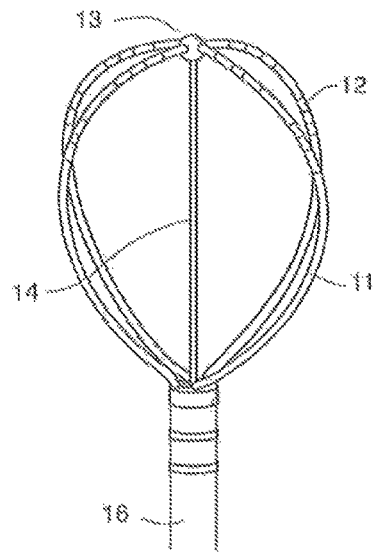
Figure 3:
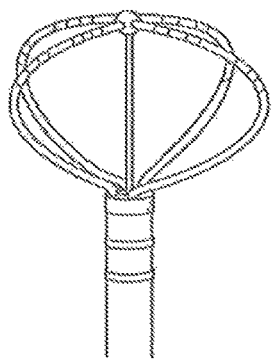
Figure 3:
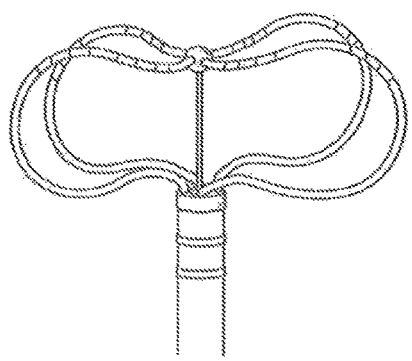

In the embodiment of FIG. 3A, the electrode assembly 10 has four spines 11. The dashed lines illustrate different stages of collapse of the electrode assembly 10 from the expanded profile by selectively and slidably move the adjusting member 14. In this embodiment, the proximal ends of spines 11 are connected to a base socket support member 18 at the distal end of the shaft 16. The base socket support member 18 provides structural support to secure the plurality of spines 11 to the shaft 16, while allowing pivotal movement of individual spines 11 during expansion and during collapse of the electrode assembly 10.

As seen in FIG. 2A, a flat wire 15 is provided in the shaft 16 for bi-directional deflection of the shaft 16. In the embodiment shown, the flat wire 15 does not extend through the distal end of the shaft 16, and is contained within shaft 16. Additionally and optionally, shaft electrodes 19 are disposed near the distal end of the shaft 16 for visualization and/or mapping purposes as used, for instance, in the EnSite™ system available from St. Jude Medical.

FIGS. 3B-3D illustrate the electrode assembly 10 at different stages of collapse or expansion as the adjusting member 14 moves forward and backward along the longitudinal direction of the shaft 16. The electrode assembly 10 has spines 11 formed of generally linear spine segments. There are two spine segments separated by an elbow region 20 in an intermediate position between the distal end and the proximal end of the embodiment shown. A distal segment extends from the elbow 20 to the distal end connected to the tip junction 13. A proximal segment extends from the elbow 20 to the proximal end connected to the support member 18. In this embodiment, electrodes are disposed between the elbows 20 and the distal ends of the spines 11. The elbow 20 bends outwardly relative to the proximal end and the distal end of the spine 11. The elbow 20 has at least one discontinuity in stiffness that allows it to bend. The at least one discontinuity may result from one or more of a change in material, a change in cross-sectional arrangement (e.g., shape), and a change in cross-sectional area. In a specific embodiment, the cross section of the spine 11 changes from the proximal segment to a less stiff cross section at the elbow 20 (by reducing the area and/or the shape of the cross section) and then changes back to the same cross section in the distal segment as in the proximal segment. The elbow 20 may be located in the mid portion of each spine 11. The location of the elbow 20 affects the size of the area A of the electrode array in this embodiment (see circle A in dash line in FIG. 2A), and defines the shape of the electrode assembly or basket 10. The elbow region 20 may be selected for each spine 11 to define a desired shape and size of area A for the electrode array, for instance, based on the type and shape of the target tissue.

Other configurations of the electrode assembly or basket 10 are possible. For example, FIGS. 3E-3G show spines 11 without elbow regions, and the spines 11 bend in an arcuate manner in response to movement of the adjusting member 14. As a result, a generally oval or spherical shape is formed instead of a conical or diamond shape.

FIGS. 4A-4D illustrate various configurations of internal support members of the spines 11 that define the deflection characteristics of the spines 11 according to different embodiments. In these embodiments, each spine 11 has an internal support member 21 embedded in a shell typically having a circular cylindrical shape. The internal support member 21 provides structure integrity and defines elbow regions for spine deflection. Each support member 21 shown supports two opposing spines 11 that are joined at the tip junction 13. Referring to the four diamond-shaped internal support members 21 in FIGS. 4A-4D, the topmost point 22 of the diamond is where tip junction 13 is located. The two terminal ends 23 of the internal support members are secured to base socket support member 18. The distal segment 24 is disposed between the elbow region 25 and the topmost point 22, and the proximal segment 26 is disposed between the elbow region 25 and the terminal ends 23. The topmost point 22 has a bent shape that can be achieved by a discontinuity (similar to the elbow 25) or by use of a shape memory material. An optional bent knee 29 is provided near each terminal end 23. The elbows 25 are characterized by a change or discontinuity in cross-sectional shape and area. Unlike a hinge, the elbow 25 in these embodiments is typically not a point but a region that includes the discontinuity in stiffness. In other embodiments, the elbow 25 will appear more like a point if the discontinuity is formed by a hinge or hinge-like mechanism.

Figure 4:
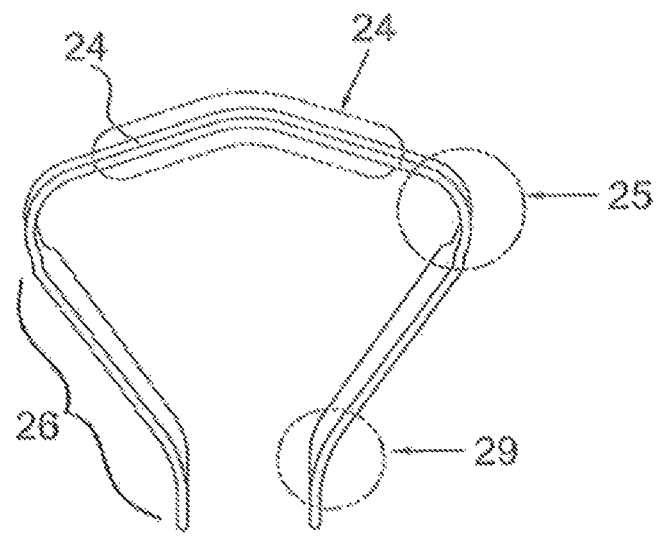
FIGS. 4A-4D illustrate various configurations of internal support members of spines according to different embodiments.
Figure 4:
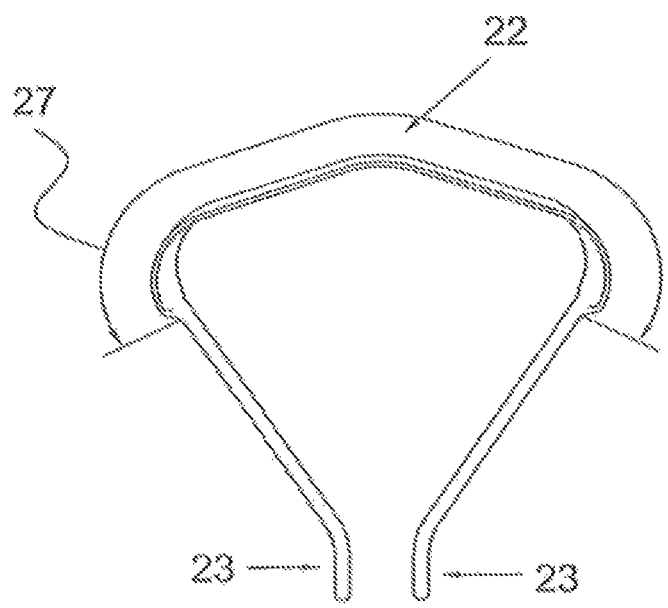
Figure 4:
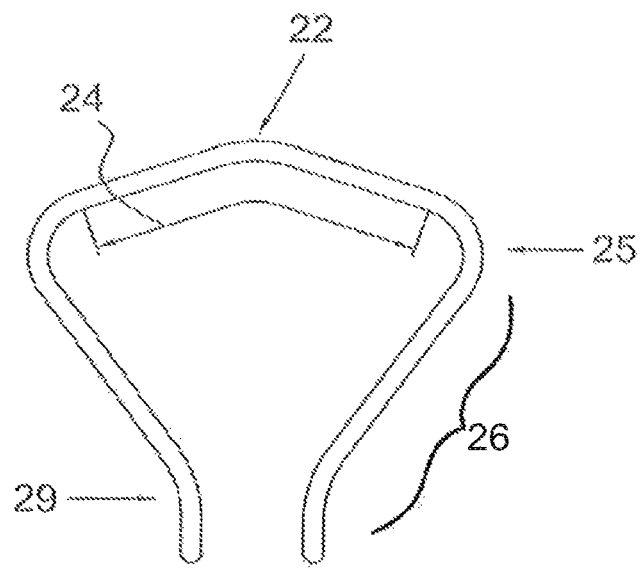
Figure 4:
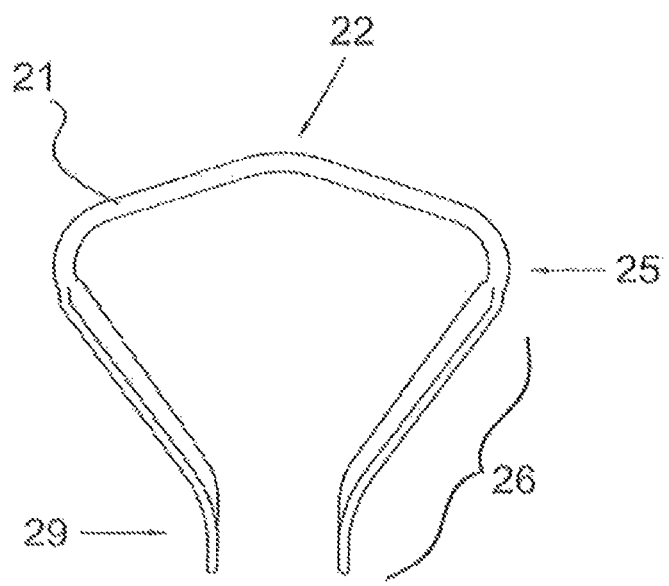

More specifically, FIG. 4A shows an internal support member 21 that has a flat, rectangular cross-sectional shape throughout. The proximal segment 26 is wider than the distal segment 24 (and has a larger cross-sectional area), and is thus structurally stronger against deflection. In some embodiments, the proximal segments 26 may be sufficiently sturdy so that when the array of electrodes are pressed against tissues with ridges or irregularities on the surface of the tissue, the proximal segments 26 do not bend out of shape but support and maintain the contact between the array of electrodes and the tissue surface. Such a design maintains the integrity of the electrode assembly 10 such that its shape is not changed when pressed upon ridges on the tissue surface.

In other embodiments, the distal segments 24 are relatively stiffer than the rest of the support member 21, so that at least when the electrode assembly 10 is in an expanded profile, the distal segments 24 remain substantially straight. In yet other embodiments, the support member 21 may have a generally uniform cross section except at the elbows 25 (and optionally the topmost point 22) where the cross section is reduced in size or otherwise shaped to provide a discontinuity in stiffness or weaker area to facilitate deflection. As mentioned, a hinge mechanism or the like may also be employed at the discontinuity.

In FIG. 4B, the internal support member 21 has a flat, rectangular cross-sectional shape in the distal segments 24 and in the elbow region 25 only. The distal segments 24 and the elbow region 25 can be referred to as a tapered section 27, which is generally of a thinner and flatter profile than proximal segments 26. The proximal segments 26 in FIG. 4B have a generally round cross-sectional shape, and are sized to be structurally stiffer against bending than the elbow region 25.

In FIG. 4C, the internal support member 21 has a generally round cross-sectional shape throughout. The proximal segments 26 are larger in diameter than the distal segments 24 and the elbow region 25. Alternatively, the entire internal support member can have a round cross-sectional shape, except at the angled points (elbow region 25 and topmost point 22) wherein a flat, rectangular cross-sectional shape or the like is provided to enhance pivotal bending at those angle points.

In FIG. 4D, the internal support member 21 has a generally round cross-sectional shape in the distal segments 24 and the elbow region 25. The proximal segments 26 have a generally flat, rectangular cross-sectional shape that is configured to be structurally stiffer than the distal segment 24 and the elbow region 25.

Although specific shapes of internal support member 21, spines 11, tip junction 13, and base socket support member 18 are disclosed for the collapsible electrode assembly 10, one of ordinary skill in the art will recognize there are other ways to build a collapsible assembly. For example, instead of providing a unitary internal support member 21 that passes through a tip junction 13 to form opposing spines 11, one can use two opposing internal support members 21 for the two opposing spines 11 that are connected at the tip junction 13 by welding or the like. In addition, the cross-sectional shapes and configuration of the internal support members 21 described may readily be modified as dictated by the functional needs of providing sufficient structure integrity, allowing deflection in the elbow region 25 and other designated regions, and providing sufficient stiffness in the distal segments 24 to ensure that the distal segments 24 remain substantially straight during ablation/mapping of tissue. Different thicknesses can also be utilized in different areas along the support member 21 to achieve the desired deflection. For example, the elbow region 25 and the topmost point 22 can be thinner or otherwise made structurally more tenuous than other parts of the support member 21, such that the desired bending occurs at the elbow regions 25 and the topmost point 22, and not in other parts of the support member 21.

In specific embodiments, the spines 11 are generally evenly spaced in the electrode assembly or basket 10 to form a stable and sturdy structure that allows the electrode array to maintain its shape during use. This is particularly helpful if the electrode array is adapted to contact body tissue having ridges or an otherwise uneven surface (e.g., cardiac tissue of the heart). One contemplated way of providing sufficiently sturdy spines 11 is to use flat internal support members 21 that only bend bi-directionally. In this way, the electrode assembly 10 can expand and collapse, but the spines 11 will not move from side to side. Another contemplated design is to have internal support members 21 made of sufficiently stiff material such that side-to-side movement is minimized. Optionally, using a tip junction 13 that aligns each spine 11 in position can help in ensuring that the array of electrodes are not affected by ridges at the target tissue site.

In use, the internal support members 21 are embedded within shells of the spines 11. When the spines deflect between the collapsed and expanded profiles, the elbow regions 25 bend while the distal segments 24 and the proximal segments 26 remain substantially straight. During expansion of the electrode assembly 10, the spines 11 form angular configurations as shown in FIGS. 3B and 3C to reach the expanded profile of FIG. 3D.

In addition to, or as an alternative to structural variations in the inner support member 21, the inner support member 21 may use material variation along the length of the support member 21 to cause the desired deflection at the elbow regions 25. Furthermore, shape memory alloy such as Nitinol may be used to facilitate bending at the elbow region 25 and may also be adapted to bias the inner support member 21 toward the expanded profile when the force that is applied to collapse the electrode assembly 10 is removed.

Other embodiments that do not employ inner support members 21 embedded within the spines 11 are expressly contemplated. In those embodiments, the spines 11 may be modified so that deflectability is a direct result of the structural and/or material variation of the spines 11 themselves. In those embodiments, the spines 11 can have shapes and material make-up similar to those described above for the internal support members 21. For example, the spines 11 can have shapes similar to those of the support members 21 as depicted in FIGS. 4A-4D.

In yet another embodiment, the expansion and collapse of the electrode assembly 10 can be controlled without using an adjusting member 14. In one alternative design, no adjusting member is needed. Instead, the electrode assembly 10 is biased toward the expanded profile when the force that is applied to collapse the electrode assembly 10 is removed. This can be achieved, for instance, by using a shape memory material such as Nitinol for the spines 11. In another alternative design, an adjusting member may be embedded in at least one of the spines 11 or a pair of opposing spines 11 (in the same manner as the internal support member 21). The embedded adjusting member can be used to adjust the expansion and collapse of the electrode assembly 10, while optionally a shape memory material or the like may be used to bias the electrode assembly 10 toward the collapsed profile. Furthermore, the embedded adjusting member may optionally be used to tilt the electrode assembly 10 relative to the shaft 16.

While the electrode assembly 10 has been discussed in detail above, the following relates to the directional control of the electrode assembly 10 as effected by tilting movement of the electrode assembly 10 relative to the shaft 16 as well as tilting of the shaft 16. As shown in FIG. 2A, the flat wire 15 is disposed within the shaft 16 for bi-directional deflection of the shaft 16. One of ordinary skill in the art will recognize that other types and shapes of wires can be used in place of, or in addition to, the flat wire 15 to effectuate the same unidirectional, bidirectional or multi-directional deflection. FIGS. 6A and 6B are side views of two catheter shafts showing different degrees of shaft deflection. FIG. 6A shows a larger degree of deflection than FIG. 6B.

In yet another embodiment, the adjusting member 14 can optionally be deflectable, much like the flat wire 15, or with the help of an additional flat wire (not shown) or guide wire (not shown). Referring to FIG. 7, by making the adjusting member 14 user-selectively deflectable, a user can tilt the electrode assembly 10 and control the degree and direction of the tilt by deflecting the adjusting member 14. In that case, the adjusting member 14 may be formed as a flat wire.

In still another embodiment, the flat wire 15 within the shaft 16 controls tilting of the shaft 16, while a deflectable adjusting member 14 controls tilting of the electrode assembly 10 relative to the shaft 16. This can be referred to as a dual distal deflection design, allowing the user to separately tilt the electrode assembly 10 (as shown in FIG. 7) and also tilt the shaft 16 in another direction (as shown in FIGS. 6A and 6B). This combination provides enhanced maneuverability and dexterity of the electrode assembly 10 of the basket catheter.

In various embodiments, the spines or arms of an expandable catheter basket may have different configurations than those discussed above. For example, referring to FIG. 8, a catheter may generally comprise a basket 110 including a plurality of arms, where each arm comprises a bendable support member 121 defining a distal portion 124, a proximal portion 126, and an intermediate portion 125 therebetween. The bendable support members 121 may comprise any number of elastic materials, such as metals and/or plastics, for example. In various embodiments, the support members 121 may be formed from superelastic or shape memory material, such as Nitinol, and/or a polymer, such as polyimide. When expanded, as shown, the basket 110 may define an expanded shape for supporting one or more electrodes that can be used in contact and/or non-contact mapping of intracardiac potentials, for example. More detail on such mapping can be found in U.S. Pat. No. 7,831,288, titled METHOD FOR MAPPING POTENTIAL DISTRIBUTION OF A HEART CHAMBER, hereby incorporated by reference as though fully set forth herein.

Figure 8:
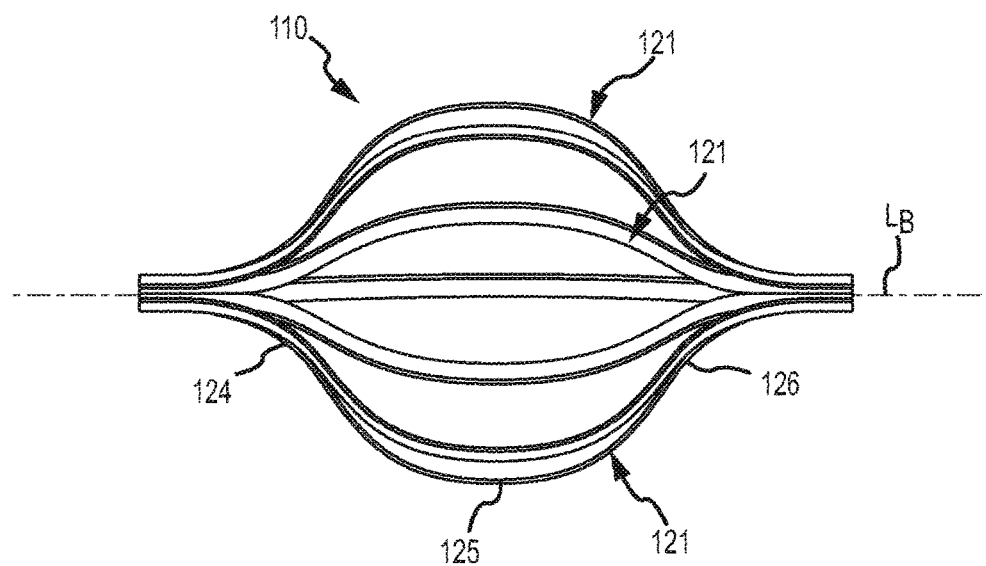
FIG. 8 is a side view of a set of bendable support members of a basket catheter in an expanded configuration, according to at least one embodiment.
Figure 9:
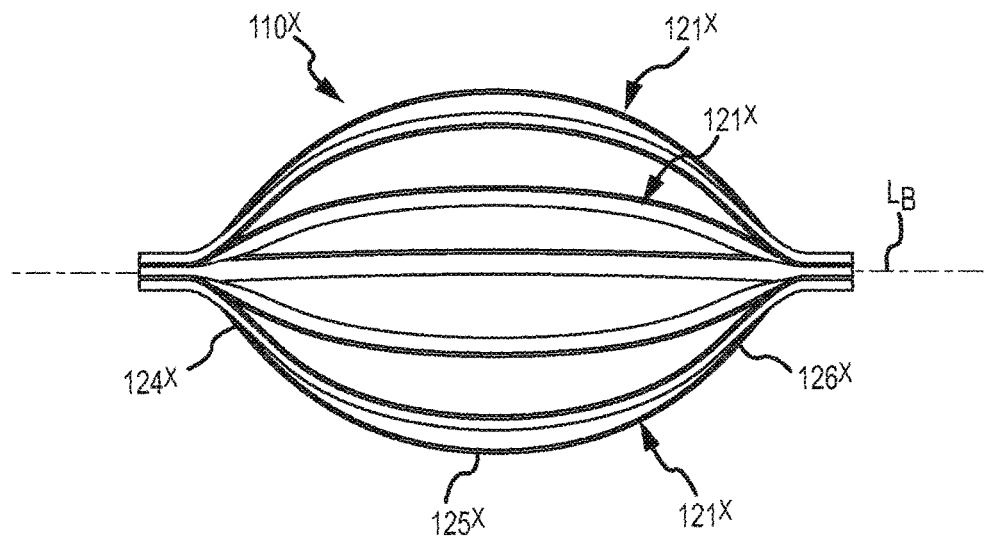
FIG. 9 is a side view of another set of bendable support members of a basket catheter in an expanded configuration, according to at least one embodiment.

Referring now to FIG. 9, the shape formed by an expanded basket, such as basket $110^X$, may be varied from that shown in FIG. 8. For example, the bendable support members $121^X$ of FIG. 9 may splay or bow outwards further near their ends and/or more uniformly from the basket's longitudinal axis $L_B$ than that shown in FIG. 8 due to variance in the flexibility or stiffness of the arm $121^X$ over its length. In other words, while the support members 121 shown in FIG. 8 may have a relatively constant measure of flexibility over each one's length, the distal portion $124^X$ and/or the proximal portion $126^X$ of at least one of the bendable support members $121^X$ shown in FIG. 9 may have an enhanced or increased measure of flexibility compared to the flexibility of the intermediate portion $125^X$ such that the distal and/or intermediate portions $124^X$, $126^X$ of the support member $121^X$ (FIG. 9) bend outwardly further than those of a comparable support member 121 (FIG. 8). In at least one embodiment, the support members $121^X$ may be similar or nearly identical to one another in terms of their longitudinal flexibility to provide a basket $110^X$ having an expanded shape that is symmetric about its longitudinal axis as shown in FIG. 9, for example.

Figure 10:
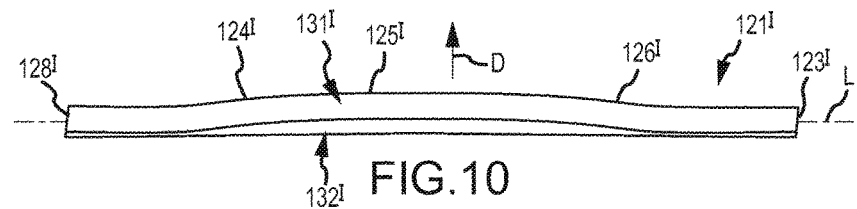
FIG. 10 is a side perspective view of one of the bendable support members of FIG. 9.

Referring now to FIG. 10, a bendable support member $121^I$ may be seen in more detail in its straight, unbent form. In addition to that described above, support member $121^I$ may comprise an elongated body defining distal end $128^I$, proximal end $123^I$, and longitudinal axis L. The flexibility of the distal and/or proximal portions $124^I$, $126^I$ may be enhanced relative to the intermediate portion $125^I$ due to the distal and proximal portions $124^I$, $126^I$ being tapered or sloped on a first side, such as top side $131^I$, of the support member $121^I$. Notably, a second side opposing the first side, that is bottom side $132^I$, may be straight and untapered. The distal portion $124^I$ and/or proximal portion $126^I$ may be tapered or sloped from the thicker intermediate portion $125^I$ towards the thinner portion of the support member at the ends $128^I$ or $123^I$ over the distal or proximal portions $124^I$, $126^I$, respectively. Additionally, such a tapering of the distal portion $124^I$ and/or proximal portion $126^I$ may provide a gradual slope to minimize stress risers when the support member's ends $128^I$, $123^I$ are compressed towards one another such that the intermediate portion $125^I$ deflects outward, in the direction of arrow D, for example.

Alternatively and although not shown, the flexibility of the distal and proximal portions of a bendable support member may be enhanced relative to the intermediate portion by adding a stiffener layer, such as polyimide, for example, to form the intermediate portion. A base layer of the support member, to which the stiffener layer may be added, may also be polyimide, for example. Thus, a bendable support member may have a varying thickness created from the same material, where the thicker portion is created by adding a stiffener layer of the same material as a base layer. In such an embodiment, the distal and/or proximal portion may have a length of approximately 0.7670 inches and the intermediate portion, over which a stiffener may be added, may have a length of approximately 0.8000 inches, with a total support member length of approximately 2.3 to approximately 2.4 inches. In at least one embodiment, the total support member length may be approximately 2 inches.

Figure 11:
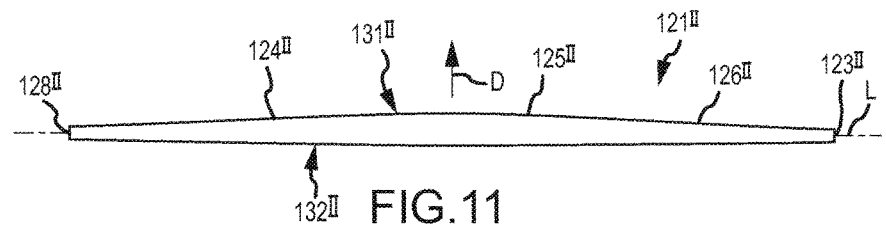
FIG. 11 is a side perspective view of another bendable support member, according to at least one embodiment.

While only one side of the support member $121^I$ may be tapered, other embodiments are contemplated. For example, a bendable support member, such as support member $121^{II}$ illustrated in FIG. 11, may include distal and proximal portions $124^{II}$ and $126^{II}$ that may be tapered on their opposing sides $131^{II}$ and $132^{II}$, respectively, thereby providing a support member with additional flexibility over such portions. The support member $121^{II}$ may be generally similar to support member $121^I$ described above in that it also includes distal and proximal ends $128^{II}$ and $123^{II}$, respectively, and is configured such that during expansion, the intermediate portion $125^{II}$ deflects outwards, generally in the direction of arrow D when the support member's ends $128^{II}$, $123^{II}$ are compressed towards one another.

Figure 12:
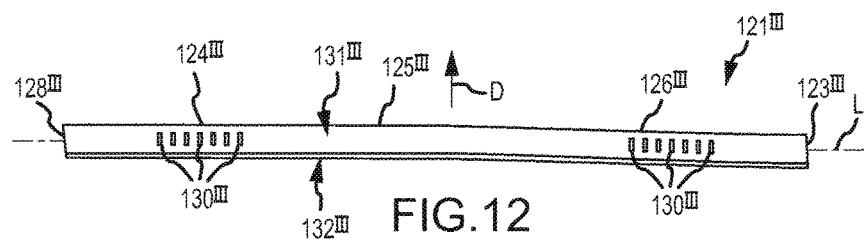
FIG. 12 is a side view of another bendable support member, according to at least one embodiment.

In addition to varying the thickness of a support member over its length to affect the shape of the support member when expanded or deflected, other embodiments are contemplated. For example, a bendable support member, such as support member $121^{III}$ illustrated in FIG. 12, may include slots or openings $130^{III}$ in the distal and/or proximal portions $124^{III}$ and $126^{III}$, respectively. The lack of material in the openings $130^{III}$ allows the support member $121^{III}$ to be more flexible in the distal and proximal portions $124^{III}$, $126^{III}$ than in the intermediate portion $125^{III}$. The support member $121^{III}$ may be generally similar to support member $121^I$ described above in that it also includes distal and proximal ends $128^{III}$ and $123^{III}$, respectively, and is configured such that during expansion, the intermediate portion $125^{III}$ deflects outwards, generally in the direction of arrow D when the support member's ends $128^{III}$, $123^{III}$ are compressed towards one another.

Figure 13:
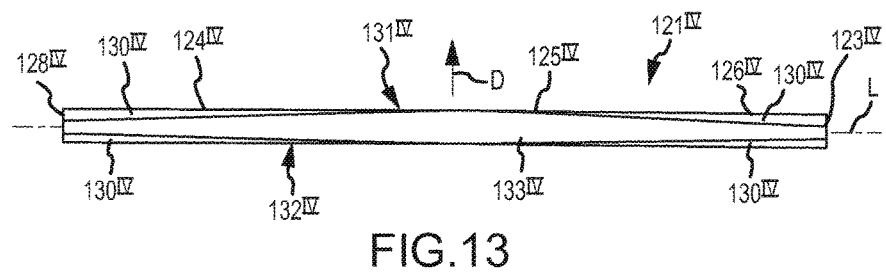
FIG. 13 is a side view of another bendable support member, according to at least one embodiment.

In another exemplary embodiment, a support member, such as support member $121^{IV}$ illustrated in FIG. 13, may include composite materials in the distal and/or proximal portions $124^{IV}$ and $126^{IV}$, respectively, which provide increased flexibility in such portions relative to the intermediate portion $125^{IV}$ therebetween. In such an embodiment, the distal and proximal portions $124^{IV}$, $126^{IV}$ may each comprise an outer or first layer of material $130^{IV}$ and an inner or second layer of material $133^{IV}$. The first layer $130^{IV}$ may comprise a first material, such as polyimide or other polymer, and the second layer $133^{IV}$ may comprise a second, different material, such as Nitinol, Nitinol wire, metallic braids, and/or a material having a different durometer than the first material, for example. Additionally, the second layer $133^{IV}$ may have a shape similar to the support member $121^{II}$ seen in FIG. 11 and discussed above. Thus, the second layer $133^{IV}$ may form the majority of the material composition of the intermediate portion $125^{IV}$, whereas the distal and proximal portions $124^{IV}$, $126^{IV}$ may comprise a material composition comprised more of the first material than the second material. The first material may be more flexible than the second material and therefore provide enhanced flexibility to the distal and/or proximal portions $124^{IV}$ and $126^{IV}$ respectively. Additionally, owing to the layers of materials, the support member $121^{IV}$ may have a consistent thickness and/or width along its length even though the flexibility of the support member $121^{IV}$ is varying over the support member's length.

As mentioned above, one or more arms of an expandable catheter basket may comprise at least one electrode through which a support member may pass. In various embodiments, each arm may comprise multiple electrodes spaced along the entire length of the arm. For example, in at least one embodiment, a first electrode may be positioned at or over a segment of the distal portion of the arm's support member, a second electrode may be positioned at or over a segment of the intermediate portion of the arm's support member, and a third electrode may be positioned at or over a segment of the proximal portion of the arm's support member. Additionally, a support member may be inserted through the electrodes such that there are multiple electrodes at one or more of the distal, intermediate, and proximal portions. The electrodes along an arm or along each of the arms may be the same or different in size. In at least one embodiment, the electrodes along each arm may be the same size, which may enhance the non-contact mapping capabilities of an expandable catheter basket.

Figure 14:
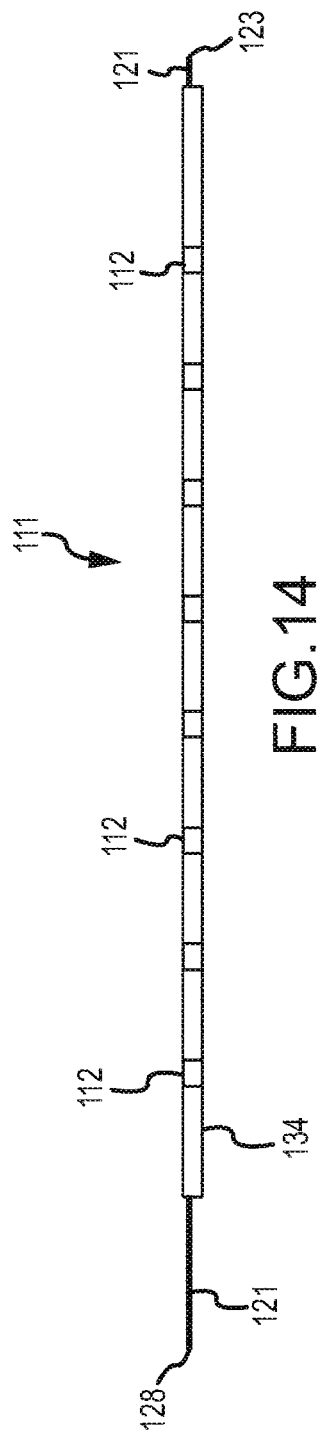
FIG. 14 is a side view of an arm of a basket catheter, according to at least one embodiment.

For example, referring to FIG. 14, a basket arm 111 is shown with a bendable support member 121 inserted through a shell or jacket 134 including electrodes 112. Wires connected to the electrodes have been omitted for clarity. The jacket may comprise a flexible polymer, such as a polyether block amide ("PEBA") or similar plastic material, for example. Support member 121 shown in FIG. 14 may be any of the support members described herein, such those shown in FIGS. 10-13 (described above) or FIG. 16A (described below), for example. As can be appreciated, the shape of the support member 121 when expanded or deflected will cause the jacket 134 and the electrodes 112 positioned along the support member 121 to similarly deflect into an expanded configuration. Accordingly, by varying the shape of the support member when in an expanded configuration as discussed above, the spacing of electrodes 112 from electrodes on other arms of the expandable catheter basket may be optimized.

Figure 15:
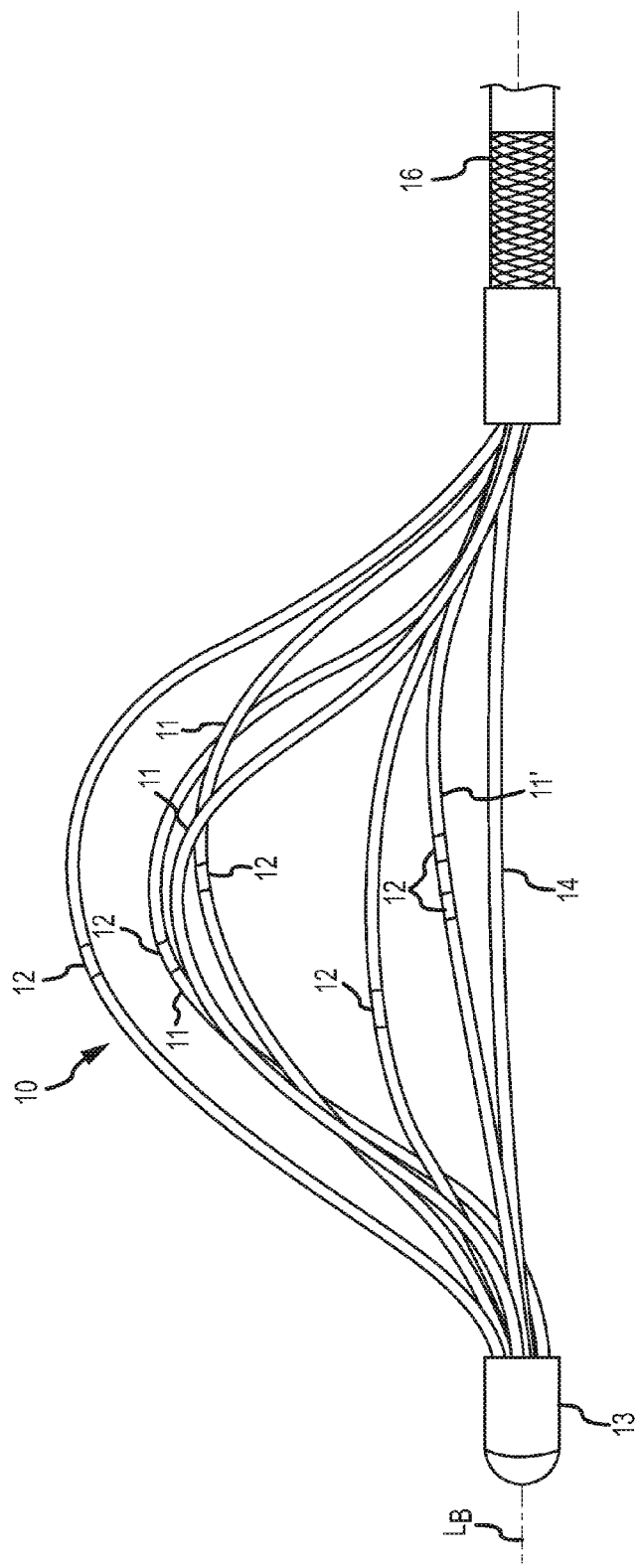
FIG. 15 is a side view of an expanded catheter basket with at least one arm inverted.

While the variance of arm and/or support member flexibility may allow for differing expanded basket shapes, such variance may also be utilized to further enhance a catheter's performance during a surgical procedure. For example, referring to FIG. 15, an expandable catheter basket 10 and related components are shown. The catheter basket 10 may be similar to that shown in FIG. 3E and described above in that an adjusting member 14 is shown having pulled a tip junction 13 toward a shaft 16 to cause the catheter basket 10 and arms 11 to attempt to deflect into an expanded configuration. However, while the catheter basket 10 may generally be in an expanded configuration, at least one of the arms, such as arm 11', is shown in an inverted state. This inverted state may occur during a procedure such that the arm 11' splays inward, toward and/or past the longitudinal axis $L_B$ of the shaft 16, control wire 14, and/or tip junction 13. In at least one embodiment, the inversion of a basket's arms may be minimized by configuring the arms to resist inversion, thereby helping keep the electrodes 12 spaced apart from one another at a desired distance during a surgical procedure. In at least one embodiment, an arm may be so configured by providing a support member with enhanced flexibility near its middle region as compared to its end regions.

Referring now to FIG. 16A, a top view of a bendable support member 221 of an arm of a catheter basket is shown. The support member 221, when assembled in a catheter basket, may be configured to deflect in or out of the plane of the page of FIG. 16A, in other words, towards or away from the viewer. The support member 221 may comprise a distal portion 224, a proximal portion 226, and an intermediate portion 225 therebetween and define a longitudinal axis L. Further, in at least one embodiment, the width of the support member 221 may vary along its length such that it is narrower or thinner near or about its middle region.

In more detail, FIGS. 16B, 16C, and 16D illustrate cross-sections of the support member 221 taken along lines 16B-16B, 16C-16C, and 16D-16D, respectively, where each line defines a plane transverse to the longitudinal axis L (see FIG. 16A). In these figures, cross-hatching has been omitted for the purposes of clarity. As can be seen, the distal portion 224 may define a rectangular, first cross-sectional shape having a first width $w_1$ and a first height $h_1$ (FIG. 16B), the intermediate portion 225 may define a rectangular, second cross-sectional shape having a second width $w_2$ and a second height $h_2$ (FIG. 16C), and the proximal portion 226 may define a rectangular, third cross-sectional shape having a third width $w_3$ and a third height $h_3$ (FIG. 16D). The height of the support member may be relatively uniform, thus, the first, second, and third heights $h_1$, $h_2$, and $h_3$ may be approximately equivalent to each other. However, the first and third widths $w_1$ and $w_3$, respectively, may each be greater than the second width $w_2$. Additionally, the first and third widths $w_1$ and $w_3$ may be approximately equivalent to each other when measured at similar distances from the distal and proximal ends, 228 and 223, respectively, of support member 221. Accordingly, the first and third cross-sectional shapes (FIG. 16B) may each define a contiguous area that is greater than the area defined by the second cross-sectional shape and the area of the first and third cross-sectional shapes may be approximately the same.

In terms of overall shape of the support member 221, at least the intermediate portion 225 may be curved inward on at least one side of the intermediate portion 225 to minimize stress risers and the like. As shown, the distal, intermediate, and proximal portions 224, 225, and 226, respectively, are curved inward on two opposing sides 241 and 242 to form an hourglass-like shape. Further, the sidewalls on both sides 241 and 242 may define parabolic profiles over the intermediate portion 225 and/or the distal and proximal portions 224, 226 when viewed from a top (or bottom) view as shown in FIG. 16A. In at least one embodiment, the narrowest width of the support member 221, when viewed from the top, occurs at the midpoint of the support member 221. For clarity, the plane defined by line 16C-16C in FIG. 16A occurs at the midpoint of the support member 221, that is, halfway between the ends 228 and 223. More specifically, in at least one embodiment, the minimum or second width $w_2$ is approximately 0.007 inches, and the first and third widths $w_1$ and $w_3$, when measured at or near the distal and proximal ends 228 and 223, respectively, are each approximately 0.013 inches. Also, the length of the support member 221, from the distal end 228 to the proximal end 223, is approximately 2 inches.

The variance in cross-sectional shape along the length of the bendable support member 221 leads to the intermediate portion 225 having an enhanced flexibility as compared to each of the distal and proximal sections 224 and 226. The increased flexibility at the intermediate portion 225 is at least partly due to the decrease in cross-sectional area, and, hence, the amount of material available to resist bending, over the intermediate portion 225 relative to the distal and proximal portions 224 and 226. In other words, the bendable support member 221 may be narrower at or near its middle than at or near its ends 228 and 223.

In more detail, referring to FIG. 16C, the intermediate portion 225 may be configured to deflect in the direction of arrow D when the support member 221 is bent with the ends 228 and 223 (see FIG. 16A) moving closer to each other. The flexibility of a beam at a plane, such as support member 221 seen in FIGS. 16B-16D, is inversely related to its cross-sectional shape's second moment of area at those planes; stated differently: the less the second moment of area, the greater the flexibility. In bending situations such as those being presently discussed, the second moment of area of the intermediate portion 225 about the y-axis (passing through the shape's centroid or longitudinal axis L in FIG. 16C), $I_{y2}$, may be calculated approximately as follows:

$$I_{y2} = \frac{w_2 h_2^3}{12}$$

Similarly, the second moments of area of the distal and proximal sections 224 and 226 about the y-axes (seen in FIGS. 16B and 16D), $I_{y1}$ and $I_{y3}$, respectively, may be calculated approximately as follows:

$$I_{y1} = \frac{w_1 h_1^3}{12}$$

$$I_{y3} = \frac{w_3 h_3^3}{12}$$

As noted above, the second width $w_2$ is less than either of the first or third widths $w_1$ and $w_3$ and the first, second, or third heights, $h_1$, $h_2$, and $h_3$, are approximately the same. Accordingly, in at least one embodiment, the second moment of area of the intermediate portion 225 about the y-axis, $I_{y2}$, is less than the corresponding second moments of area of the distal or proximal portions 224 and 226, $I_{y1}$ and $I_{y3}$. Subsequently, the flexibility of the intermediate portion 225 is likewise greater than that of the distal or proximal portions, 224 and 226.

When the support member 221 is in a desired expanded or arched configuration (see FIG. 9, for example), the enhanced flexibility of the intermediate portion 225 relative to the distal and proximal portions 224 and 226 may allow the distal and proximal portions 224 and 226 to resist inversion while the intermediate portion 225 may not contribute much resistance, mechanically speaking, to holding support member 221 or causing the support member 221 to reside in an inverted state. Moreover, if a support member 221 did invert during use, the support member 221 may be more likely to reverse such inversion and return to the desired expanded or arched configuration owing to the enhanced flexibility at the intermediate portion 225. In other words, the intermediate portion's enhanced flexibility may allow for the inversion of any support members 221 to only be a temporary event.

Figure 17:
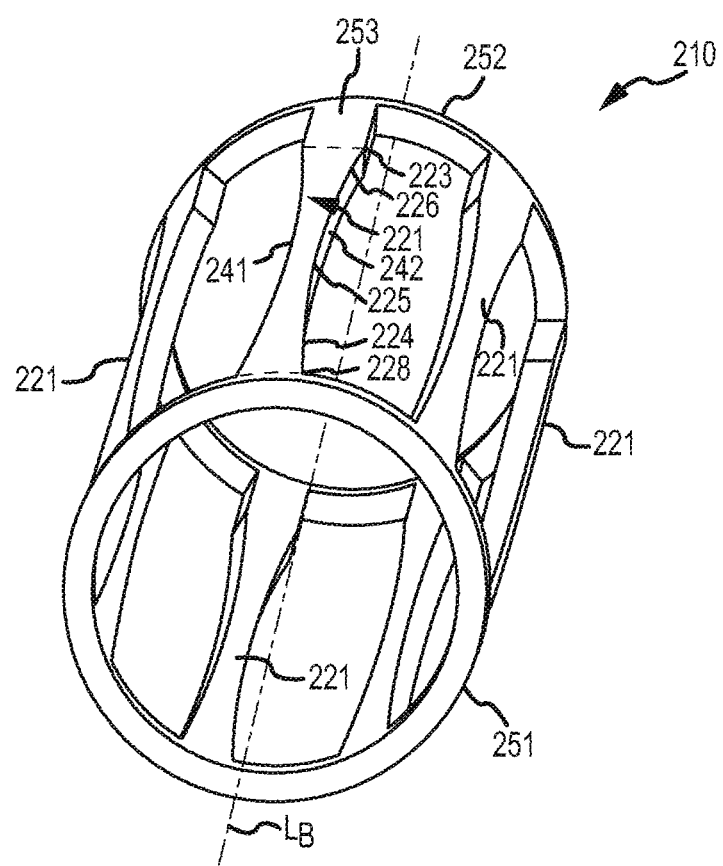
FIG. 17 is a distal perspective view of a set of bendable support members cut from a tube of material, according to at least one embodiment.

Referring now to FIG. 17, in addition to methods described above for creating the support members of an expandable catheter basket, the support members of a basket, such as basket 210, may be formed as follows. In at least one embodiment, a tube, such as a Nitinol hypotube, may be cut or formed to provide support members 221. In various embodiments, a Nitinol hypotube may have an outer diameter of approximately 0.098 inches, approximately 0.097 inches, or approximately 0.060 inches. Additionally, in various embodiments, the inner diameter may be approximately 0.089 inches (for tubes having an outer diameter of about 0.098 or about 0.097 inches) or approximately 0.050 inches (for tubes having an outer diameter of about 0.060 inches). As mentioned above, the length of a support member 221 may be about 2 inches, accordingly as illustrated in FIG. 17, a hypotube may be over 2 inches in length.

In at least one embodiment, the Nitinol hypotube may be laser cut to remove material, resulting in basket 210 seen in FIG. 17. The basket 210 may comprise support members 221 between a distal end ring 251 and a proximal end ring 252 and may define a longitudinal axis $L_B$. As discussed above, each support member 221 may comprise a distal portion 224, a proximal portion 226, and an intermediate portion 225 therebetween. Opposing sides 241, 242 of the support member 221 may be tapered or curved inward, resulting in the intermediate portion 225 being narrower than the distal or proximal portions 224, 226 as measured in a circumferential direction of the basket 210. The distal and proximal ends 228 and 223 (highlighted with dotted lines in FIG. 17) of the support members 221 may be integrally connected to the distal and proximal end rings 251 and 252, respectively. Further, the proximal end 223 of a support member 221 may be integrally coupled to the proximal end ring 252 by proximal extension 253. Although not shown, the proximal extensions 253 may be further cut transversely to remove the proximal end ring 252 from the basket 210 and provide a free end to support member 221 such that one or more electrodes and/or a polymer jacket may be slid thereover (see, e.g., FIG. 14). Afterwards, the support members 221 and/or extensions 253 may be coupled to a catheter shaft, such as shaft 16 discussed above, and the distal end ring 251 may form at least a portion of the catheter's tip, such as tip junction 13 also discussed above (see, e.g., FIGS. 3E and 15).

Figure 18:
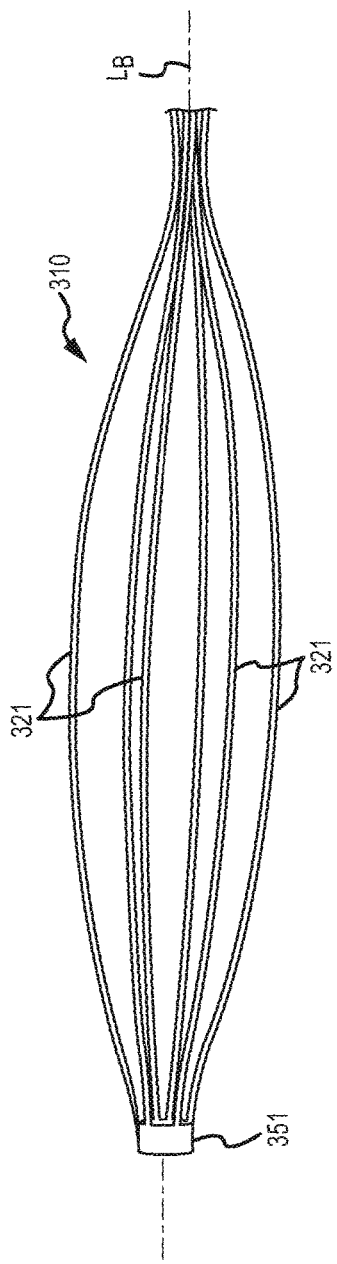
FIG. 18 is a side view of a shape-set set of bendable support members, according to at least one embodiment.
Figure 19:
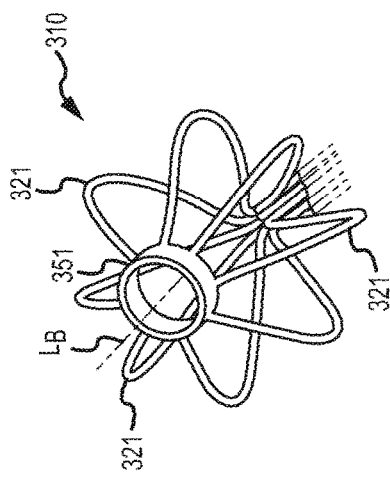
FIG. 19 is a distal perspective view of the shape-set set of bendable support members of FIG. 18.

Referring now to FIGS. 18 and 19, in at least one embodiment, support members, such as Nitinol support members 321 extending from distal end ring 351, may be biased outwards, away from the longitudinal axis $L_B$ of an expandable basket 310. To achieve such a biasing, a mandrel defining the biased shape seen in FIGS. 18 and 19 may be first inserted into the lumen defined between the support members 321, thereby elastically deflecting them towards the illustrated shape. Then, the basket 310 and mandrel may be placed into an oven and heated such that the Nitinol support members become at least partially malleable. Immediately thereafter, the basket 310 and mandrel may be placed in a cooling bath of water, thereby resulting in the support members 321 becoming heat set into the shape as shown in FIGS. 18 and 19. Accordingly, the shape-set support members 321 may be in an at least partially retracted state as shown in FIGS. 18 and 19 but may already be biased at least partially outward, away from the longitudinal axis $L_B$ to help ensure that the desired shape of the support members is achieved when fully expanded as discussed above, that is by moving the distal end ring 351 in a proximal direction.

While the foregoing has discussed the geometric narrowing of a support member to provide enhanced flexibility of the member's intermediate portion relative to its distal and/or proximal portions, it is contemplated that one or more other flexibility enhancements may be utilized in an intermediate portion of a support member. For example, slots or openings, such as openings $130^{III}$ shown in FIG. 12 and discussed above, may be added to a support member's intermediate portion in place of or in addition to the geometric narrowing of the intermediate portion. Likewise, stiffeners or composite material layers, such as layers $130^{IV}$ and $133^{IV}$ seen in FIG. 13 and discussed above, may be added to a support member to vary the material makeup of the support member over its length and provide enhanced flexibility of the member's intermediate portion relative to its distal and proximal portions. As noted above, varying materials over the length of each support member may also include using different durometer materials, selectively applying Nitinol and/or Nitinol wire, incorporating metallic braids, et cetera.

Although a number of representative embodiments according to the present teachings have been described above with a certain degree of particularity, those skilled in the art could make numerous alterations to the disclosed embodiments without departing from the scope of this invention. For example, while the bendable support members may be integrally formed from a tube, it is contemplated that the support members may be independently formed and then coupled using additional components. All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the invention as defined in the appended claims.

What is claimed is:

1. A catheter, the catheter comprising:
   an elongated body having a proximal end and a distal end; and
   an electrode assembly at the distal end of the elongated body, the electrode assembly comprising a plurality of arms, each of the arms having a proximal end connected to the distal end of the elongated body and a distal end, the distal ends of the arms being connected at a tip junction, wherein the electrode assembly is collapsible to a collapsed arrangement to fit within a lumen of a shaft and is expandable to an expanded arrangement;
   wherein at least one arm of the plurality of arms comprises:
   at least one electrode; and
   a support member comprising a first layer disposed on a second layer, the first layer and the second layer extended along the support member, wherein the support member includes a distal portion, a proximal portion, and an intermediate portion therebetween, and wherein the first layer is thicker than the second layer at the proximal portion and the distal portion, and the second layer is thicker than the first layer at the intermediate portion.

2. The catheter according to claim 1 wherein the second layer comprises a majority of a material composition of the intermediate portion.

3. The catheter according to claim 1 wherein the first layer comprises a majority of a material composition of the distal portion.

4. The catheter according to claim 1 wherein the first layer comprises a majority of a material composition of the proximal portion.

5. The catheter according to claim 1 wherein the first material is more flexible than the second material.

6. The catheter according to claim 1 wherein a thickness of the support member is consistent from the distal portion to the proximal portion.

7. The catheter according to claim 1 wherein the support member comprises a superelastic material.

8. A catheter comprising:
an expandable catheter basket comprising a plurality of arms, wherein at least one of the arms comprises:
a bendable support member defining a distal portion, a proximal portion, and an intermediate portion therebetween, wherein the thickness of the bendable support member is consistent along the distal portion, proximal portion, and intermediate portion; and
at least one electrode positioned along the support member,
wherein the bendable support member includes a first layer and a second layer, the first layer comprises a first material and the second layer comprises a second material, and the second material is thicker along the intermediate portion than along the proximal portion or distal portion.

9. The catheter according to claim 8 wherein the second layer comprises a majority of a material composition of the intermediate portion.

10. The catheter according to claim 8 wherein the proximal portion comprises a plurality of slots.

11. The catheter according to claim 8 wherein the first layer comprises a majority of a material composition of the distal portion.

12. The catheter according to claim 8 wherein the first layer comprises a majority of a material composition of the proximal portion.

13. The catheter according to claim 8 wherein the first material is more flexible than the second material.

14. The catheter according to claim 8 wherein the support member comprises a superelastic material.

15. A catheter, the catheter comprising:
an elongated body having a proximal end and a distal end; and
an electrode assembly at the distal end of the elongated body, the electrode assembly comprising a plurality of arms, each of the arms having a proximal end connected to the distal end of the elongated body, a distal end, and an intermediate portion between the proximal end and the distal end of the arms, the distal ends of the arms being connected at a tip junction, wherein the electrode assembly is collapsible to a collapsed arrangement to fit within a lumen of a shaft and is expandable to an expanded arrangement;
wherein at least one arm of the plurality of arms includes a first layer and a second layer, wherein the second layer is thicker at the intermediate portion than at the proximal portion or the distal portion, and wherein at least one arm of the plurality of arms includes a means for increasing the flexibility of the at least one arm.

16. The catheter according to claim 15, wherein the means for increasing the flexibility of the at least one arm being selected from the group consisting of a material, thickness, or tapering of the arm or the first or second layer.

* * * * *